United States Patent
Wang et al.

(10) Patent No.: US 7,206,706 B2
(45) Date of Patent: Apr. 17, 2007

(54) INSPECTION METHOD AND SYSTEM USING MULTIFREQUENCY PHASE ANALYSIS

(75) Inventors: Changting Wang, Niskayuna, NY (US); William Stewart McKnight, Hamilton, OH (US); Ui Suh, Cincinnati, OH (US); Serkan Ertekin, Istanbul (TR)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 11/210,119

(22) Filed: Aug. 22, 2005

(65) Prior Publication Data

US 2006/0217908 A1 Sep. 28, 2006

Related U.S. Application Data

(60) Provisional application No. 60/660,032, filed on Mar. 9, 2005.

(51) Int. Cl.
*G06F 19/00* (2006.01)

(52) U.S. Cl. .......................................... 702/64; 702/57

(58) Field of Classification Search .................. 702/57, 702/81, 64
See application file for complete search history.

(56) References Cited

U.S. PATENT DOCUMENTS 5,610,517 A * 3/1997 Ma et al. .................... 324/233
6,037,768 A * 3/2000 Moulder et al. ............ 324/225

FOREIGN PATENT DOCUMENTS

JP 59009552 1/1984
JP 59108955 6/1984

OTHER PUBLICATIONS

Y. Plotnikov & W.J. Bantz, "Subsurface Defect Detection in Metals With Pulsed Eddy Current," Review of Quantitative Nondestructive Evaluation, 2005, vol. 24, pp. 447-454.
C. Tai et al., "Pulsed Eddy Current for Metal Surface Cracks Inspection: Theory and Experiment," Review of Quantitative Nondestructive Evaluation, 2002, vol. 21, pp. 388-395.

(Continued)

*Primary Examiner*—John Barlow
*Assistant Examiner*—Douglas N Washburn
(74) *Attorney, Agent, or Firm*—Penny A. Clarke; Patrick K. Patnode (57) ABSTRACT

A method for inspecting a part is provided. The method includes applying a number of multifrequency excitation signals to a probe to generate a number of multifrequency response signals for the part being inspected. The method further includes performing a multifrequency phase analysis on the multifrequency response signals to inspect a subsurface of the part. An inspection system is provided and includes an eddy current (EC) probe configured to induce eddy currents in a part. The system further includes an eddy current instrument coupled to the EC probe and configured to apply multifrequency excitation signals to the EC probe to generate multifrequency response signals. The system further includes a processor configured to analyze the multifrequency response signals from the EC instrument by performing a multifrequency phase analysis, to inspect a subsurface of the part.

21 Claims, 6 Drawing Sheets

OTHER PUBLICATIONS

C. K. Sword & M. Simaan, "Estimation of Mixing Parameters for Cancellation of Discretized Eddy Current Signals Using Time and Frequency Domain Techniques," Journal of Nondestructive evaluation, vol. 5, No. 1. 1985, pp. 27-35.

M.S. Safizadeh, Z. Liu, B.A. Lepine & D. S. Forsyth, "Multifrequency Eddy Current for the Characterization of Corrosion in Multilayer Structures," Materials Evaluation, May 2004, pp. 535-539.

Robert C. McMaster et al., "Examples of Multifrequency Testing Applications," American Society For Nondestructive Testing, Second Edition, vol. 4, Electromagnetic Testing, pp. 602-603, 1986.

G. Dobmann, Lifetime Extension—The Contribution of a Low-and Multi-Frequency Eddy Current Technique to Assure the Integrity of the Cladding in Nuclear Power Plant Pressure Vessels, Pergamon, vol. 39, No. 5, pp. 235-242, 1997.

EP Search Report, EP06251183, May 24, 2006.

J. Stolte et al., "Multifrequency Eddy Current Testing of Steam Generator Tubes Using Optimal Affine Transformation," Review of Progress in quantitative Nondestructive Evaluation, vol. 7, D. O. Thompson and D. E. Chimenti, Eds. Plenum, 1988, pp. 821-830.

* cited by examiner

(1) UT 10 MHz F/6 LW scan 0.005" step          (2) EC scan 0.020" step

INSPECTION METHOD AND SYSTEM USING MULTIFREQUENCY PHASE ANALYSIS

CROSS REFERENCE TO RELATED APPLICATIONS

This application is a non-provisional application of provisional application Ser. No. 60/660032, entitled "Blind Zone Inspection with Eddy Current using Multifrequency and Phase Analysis", filed Mar. 9, 2005, which is herein incorporated by reference.

BACKGROUND

The invention relates generally to inspection techniques and more particularly to a method and system for performing subsurface defect inspections using a multifrequency phase analysis eddy current technique.

A number of different non-destructive inspection techniques have been proposed such as ultrasonic testing (UT), eddy current inspection techniques and surface acoustic techniques. Exemplary eddy current inspection techniques include pulsed eddy current techniques and multi-frequency eddy current techniques. Eddy current techniques are performed to detect anomalies in material surfaces as well as to detect anomalies deep within material surfaces. Eddy current inspection techniques are also used for inspecting coated materials.

It is desirable to inspect forged parts using non-destructive techniques such as eddy current techniques. As is known to those skilled in the art, ultrasonic testing (UT) utilizes a pulse-echo method to detect flaws inside forged materials. However, even with the use of special probes and pulser instrumentation, UT techniques generally cannot detect flaws in the region of approximately 1.5 mm or less near the surface of the material of the part to be inspected. This region is commonly referred to as the "UT blind zone."

In order to overcome the disadvantages of UT inspection and to add flexibility to the manufacturing process, 0.050 inches (or about 1.27 mm) material is added to the final part configuration. However, the addition of this material generally increases the manufacturing cost due to material waste and production time.

On the other hand, eddy current inspection techniques are capable of detecting surface and near surface defects because the electromagnetic energy is concentrated in a shallow zone at the surface. However, these techniques typically exhibit a poor signal to noise ratio (SNR) for small flaws under the surface due to an "electromagnetic skin effect," which limits the penetration of eddy currents into the material under test. The pulsed eddy current technique involves eddy current responses over a broad frequency spectrum. However, the pulsed eddy current technique typically requires complicated signal processing developments, as well as high-speed data acquisition and processing systems.

Multi-frequency eddy current techniques concentrate electromagnetic energies at a few frequencies and yield good signal to noise ratios using lock-in amplifiers. A subsurface eddy current multifrequency inspection technique that enhances the signal to noise ratio and improves the near surface detection in deeper locations within the part to be inspected, is therefore desired.

BRIEF DESCRIPTION

Embodiments of the present invention address this and other needs. In one embodiment, a method for inspecting a part is provided. The method includes applying a number of multifrequency excitation signals to a probe to generate a number of multifrequency response signals for the part being inspected. The method further includes performing a multifrequency phase analysis on the multifrequency response signals to inspect a subsurface of the part.

In a second embodiment, a method for performing subsurface defect inspections using eddy currents is provided. The method includes applying a number of multifrequency signals to an eddy current probe and generating a number of multifrequency response signals from the multifrequency signals. The multifrequency response signals are included in a multifrequency response dataset. The method further comprises identifying a reference dataset that includes at least two frequency response signals. The reference dataset is a subset of the multifrequency response dataset, and the at least two frequency signals comprise distinct frequency ranges. Then, the method further includes mixing the at least two frequency response signals to determine a number of processing parameters and applying the processing parameters to the multifrequency response signal dataset to generate a noise-filtered dataset. The method further includes performing a phase analysis on the noise-filtered dataset.

In a third embodiment, an inspection system is provided. The system includes an eddy current probe, an eddy current instrument and a processor. The eddy current probe is configured to induce eddy currents in a part for performing an inspection of the part. The eddy current instrument is coupled to the eddy current probe, and is configured to apply a number of multifrequency excitation signals to the eddy current probe to generate a number of multifrequency response signals. The processor is configured to analyze the multifrequency response signals from the eddy current instrument by performing a multifrequency phase analysis, to inspect a subsurface of the part.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
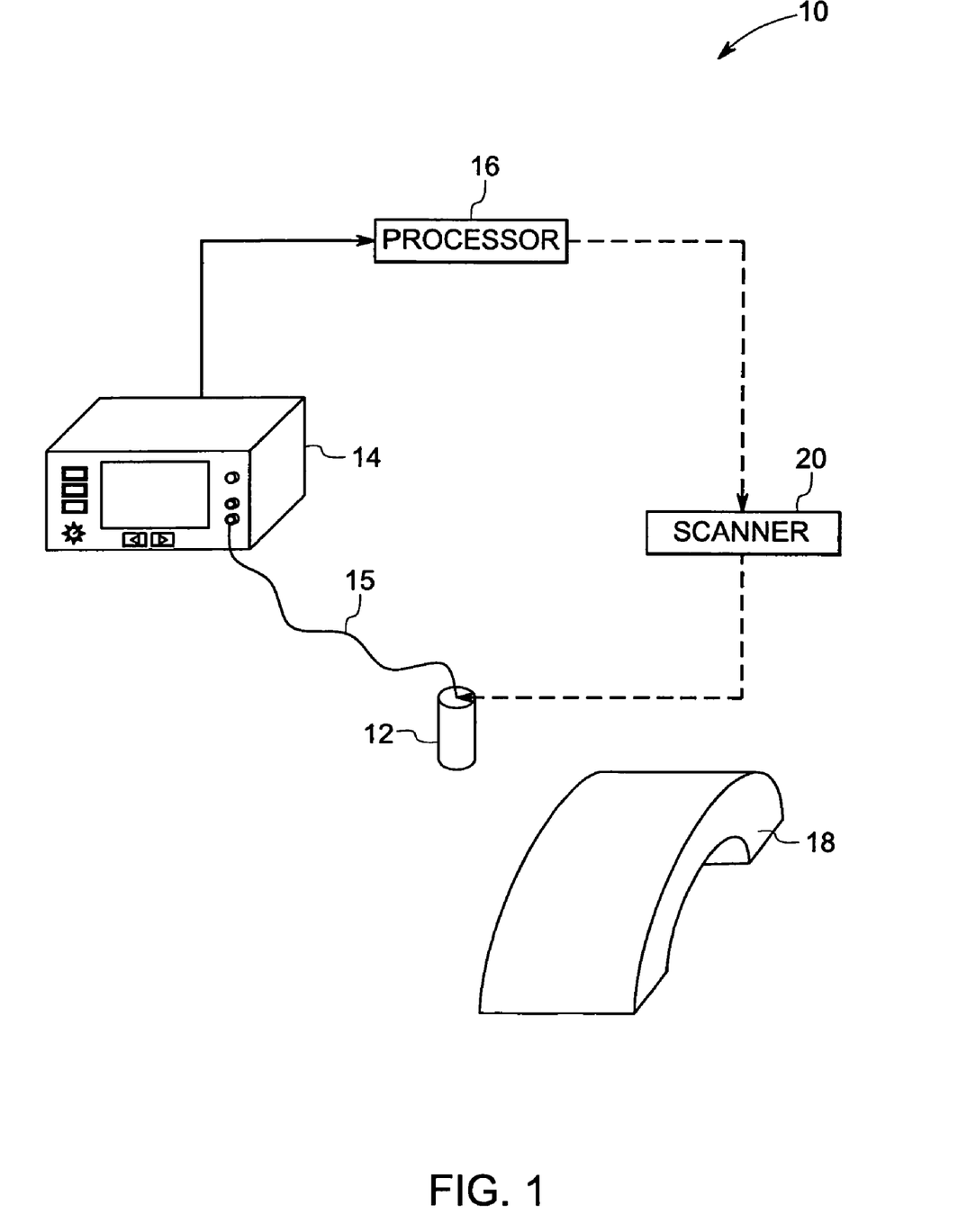
FIG. 1 is an illustration of an exemplary inspection system for performing subsurface defect inspections, in accordance with the present technique.

FIG. 1 is an illustration of an exemplary inspection system for performing subsurface defect inspections, in accordance with the present technique. As shown in FIG. 1, inspection system 10 includes an eddy current probe 12, an eddy current instrument 14 and a processor 16. The eddy current probe 12 is configured to induce eddy currents in an inspection part 18, for performing an inspection of the part 18. The probe 12 may have any conventional configuration, and is suitably coupled to the eddy current instrument 14 by an electrical cable 15, for conducting an eddy current inspection in a conventional manner. In accordance with the present embodiment, the eddy current instrument 14 is configured to apply multifrequency excitation signals to the eddy current probe 12 to generate a number of multifrequency response signals.

In certain embodiments, an eddy current inspection of the inspection part 18 may be automated by mounting the inspection part 18 and the eddy current probe 12 onto a multi-axis computer numerically controlled scanner 20. The scanner 20 may be typically configured for a three orthogonal translation axis movement of the probe 12, along the three axes X, Y, Z, with rotational motion around one or more of the three translation axes as required for the particular inspection part 18. The probe, therefore, may be accurately positioned relative to the inspection part 18 and moved along with all the required degrees of freedom in accordance with the software conventionally programmed in the scanner 20. The scanner 20 may also be controlled by an external processing unit, such as processor 16.

The processor 16 is configured to analyze the multifrequency response signals from the eddy current instrument 14. In accordance with a particular embodiment of the present technique, and as will be described in greater detail below, the processor is configured to perform a multifrequency phase analysis to detect subsurface defects within the inspection part 18. In particular, the processor 16 is configured to identify a reference dataset comprising at least two frequency response signals. The reference dataset is formed from a multifrequency response dataset. In a particular embodiment, the two frequency signals comprise distinct frequency ranges. The processor 16 is further configured to mix the two frequency response signals to determine a number of processing parameters, apply the processing parameters to the entire multifrequency response signal dataset to generate a noise-filtered dataset and perform a phase analysis on the noise-filtered dataset.

Figure 2:
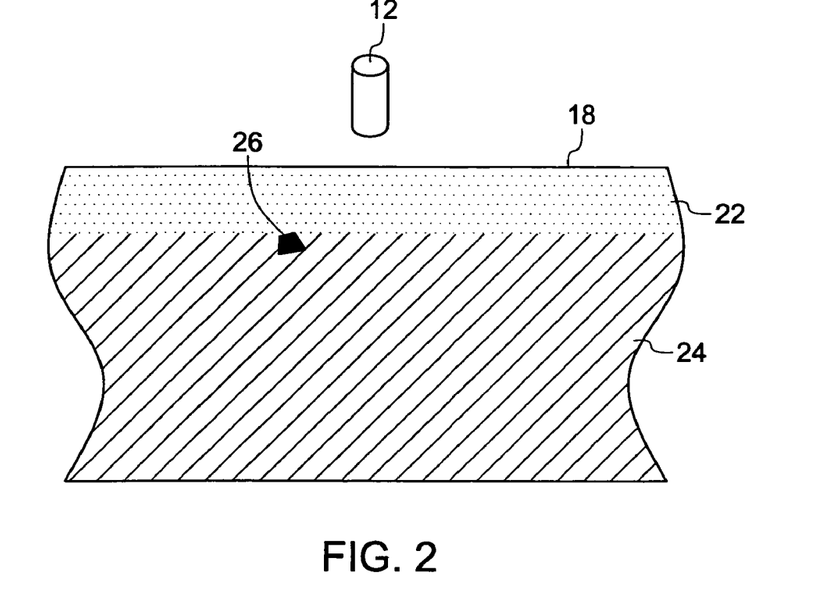
FIG. 2 is an illustration of the inspection by a probe through a coated surface in an exemplary inspection part using eddy currents.

FIG. 2 is an illustration of the eddy current inspection of an exemplary coated part. Referring to FIG. 2, the probe 12 is positioned above the inspection part 18. The inspection part 18 includes a metallic coating 22 (or other conductive coating) formed on a substrate material 24. The substrate material may comprise nickel based alloys or other conductive metals, for example. Reference numeral 26 represents a defect located under the metallic coating 22. The defect 26 may be representative of a crack, void or disbond within the inspection part 18 caused by fatigue or corrosion, resulting in a detectable change in the metallic coating 22 or in the base material of the inspection part 18. As will be appreciated by those skilled in the art, eddy current techniques are based on the principle of electromagnetic induction. Eddy currents are induced within the material under inspection by alternating magnetic fields created in the coil of an eddy current probe when the probe is moved into proximity with the material under test. Changes in the flow of eddy currents are caused by the presence of a discontinuity or a crack in the inspection part. The altered eddy currents produce a secondary field, which is received by an eddy current probe coil or by other type of sensors in the eddy current probe, which converts the altered secondary magnetic field measurement to an electrical output, which may be subsequently recorded on a strip chart. Flaws or defects may be indicated if the electrical signal exceeds a predetermined voltage threshold. An eddy current machine operator may then infer the size of flaws from the signals recorded on the strip chart or output device of the system.

Figure 3:
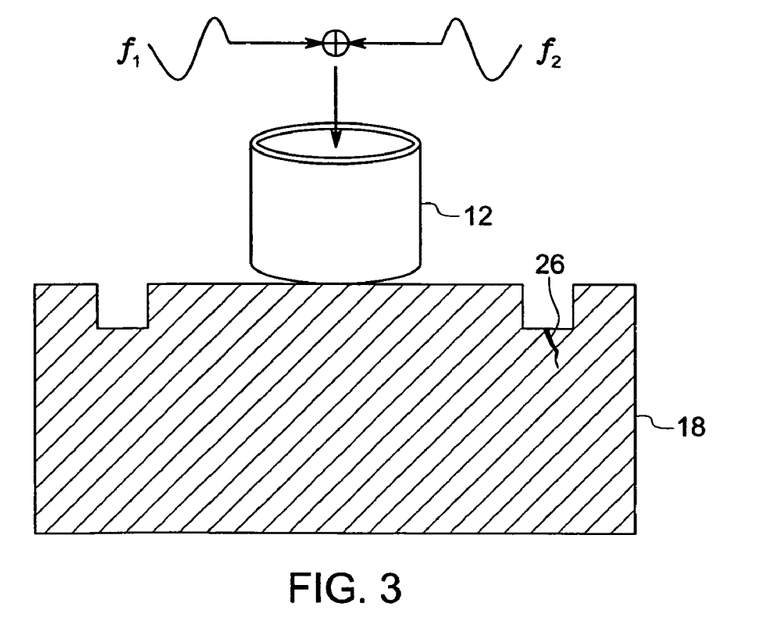
FIG. 3 is an illustration of the application of multifrequency excitation signals to a probe for inspection of an exemplary inspection part.

FIG. 3 is an illustration of the application of multifrequency excitation signals to a probe for inspection of an exemplary inspection part. Although FIG. 3 uses two eddy current frequencies, the present technique is equally applicable to other multifrequency combinations. Referring to FIG. 3, $f_1$ and $f_2$ represent two eddy current frequencies for performing a two-frequency eddy current inspection of the inspection part 18. Inspection part 18 further includes a defect or a crack 26. In accordance with embodiments of the present technique, the application of multifrequency eddy currents on the inspection part, results in the generation of different magnitude and phase eddy current responses for different frequencies. The additional information provided by the multifrequency eddy current along with phase information is used to reduce undesired signals, enhance the desired signal to noise ratio and provide additional discrimination to reduce false calls, in a manner as will be described in greater detail below.

Figure 4:
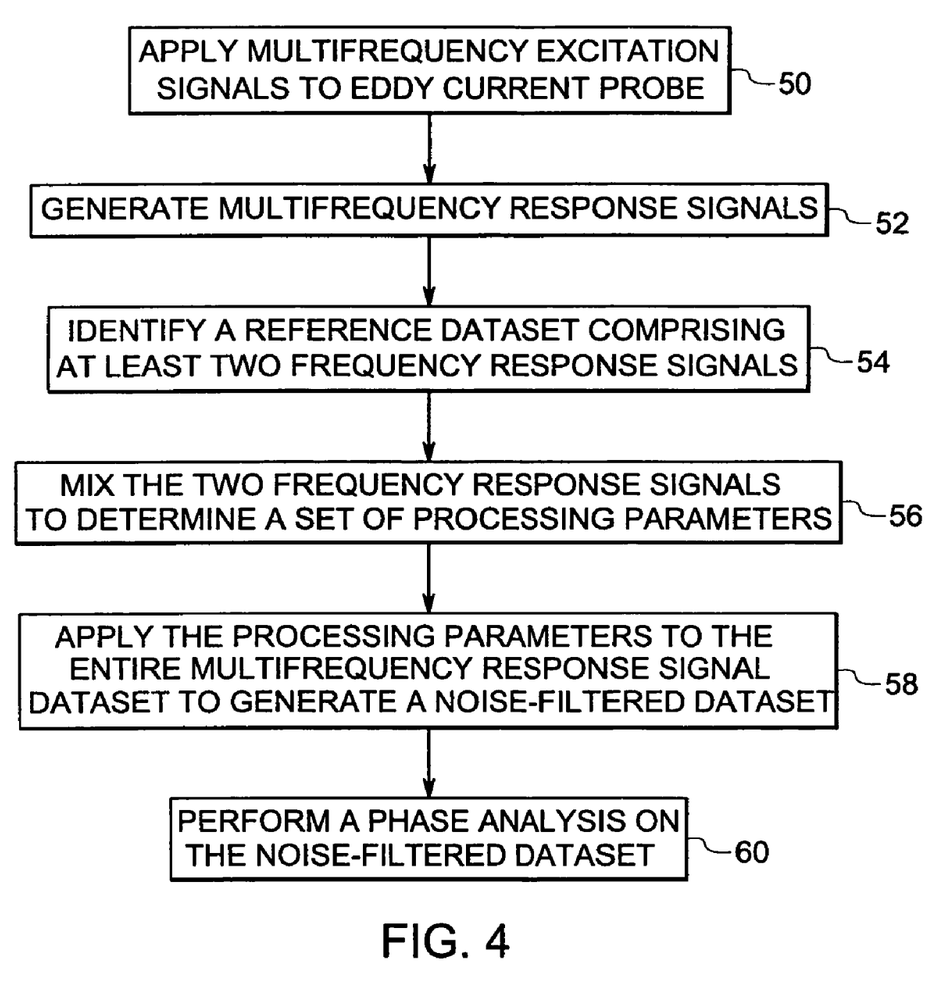
FIG. 4 is an exemplary flowchart including exemplary logic for performing eddy current subsurface defect inspections using multifrequency phase analysis, in accordance with the present technique.

FIG. 4 is an exemplary flowchart including exemplary logic for performing eddy current subsurface defect inspections using multifrequency phase analysis, in accordance with the present technique. In step 50, multifrequency excitation signals are applied to an eddy current probe to induce eddy currents in an inspection part. In step 52, multifrequency response signals are generated. The number of frequencies needed for the generation of the multifrequency response signals, may be selected based on the number of undesired noise features to eliminate. In a particular embodiment of the present invention, the selected number of frequencies is greater than the number of undesired noise features to eliminate with an assumption that, a flaw in the sample under test and any non-relevant indications to be suppressed do not cause the same phase and magnitude change in the eddy current signal at different frequencies, or alternatively, the eddy current probe response in X-Y plots at different frequencies are not collinear after a phase angle rotation. In one embodiment, the generated multifrequency response signals are included in a multifrequency response dataset. As used herein, a "multifrequency response dataset" refers to a dataset that comprises the entire set of response signals that are generated as a result of the eddy current induced in the inspection part under consideration by application of the multifrequency excitation signals to the eddy current probe.

In step 54, a reference dataset is identified from the multifrequency dataset. In accordance with the present embodiment, the reference data set refers to a dataset that is relatively free from defects but dominated by undesired noise features. Further, in accordance with this embodiment, the reference dataset comprises at least two frequency response signals, where the two frequency response signals comprise distinct frequency ranges. The two frequency response signals may be represented as follows:

$$f_1: \vec{x}_1(t) = X_d(t) \angle \theta_d(t) + X_n(t) \angle \theta_n(t) \quad (1)$$

$$f_2: \vec{x}_2(t) = k_d(t) X_d(t) \angle (\theta_d(t) + \Delta\theta_d(t)) + k_n(t) X_n(t) \angle (\theta_n(t) + \Delta\theta_n(t)) \quad (2)$$

where $f_1$ and $f_2$ represent two exemplary eddy current frequencies for a two-frequency eddy current inspection, $x_1(t)$ and $x_2(t)$ represent the eddy current response signals corresponding to the frequencies $f_1$ and $f_2$ at position (or time) t, $X_d(t)$ represents the magnitude of flaw in the response signal, $X_n(t)$ represents the magnitude of undesired noise features in the response signal, $k_d(t)$ represents a coefficient reflecting a change in the magnitude in the response signal, $k_n(t)$ represents a coefficient reflecting the change in the noise in the response signal, $\angle \theta_d(t)$ represents the phase angle of the flaw in the response signal, $\angle \theta_n(t)$ represents the phase angle of undesired noise features in the response signal, $\Delta\theta_d(t)$ represents the phase change of the flaw in the response signal and $\Delta\theta_n(t)$ represents the phase change of the undesired noise feature in the response signal. In one embodiment, the two frequencies, $f_1$ and $f_2$ are selected such that $\Delta\theta_d(t) - \Delta\theta_n(t)$ is in a range from about 135° to about 225°. In a particular embodiment, the two frequencies $f_1$ and $f_2$ are selected, such that $\Delta\theta_d(t) - \Delta\theta_n(t) = 180°$. In addition, the selection of the frequency ranges $f_1$ and $f_2$ corresponding to the multifrequency excitation signals is also based on the skin penetration desired within the inspection part 18.

In step 56, the two frequency response signals shown in equations (1) and (2) are mixed to determine a set of processing parameters. In one embodiment, the processing parameters correspond to the coefficients, $k_d(t)$ and $k_n(t)$. As will be appreciated by those skilled in the art, each of the frequency response signals $x_1(t)$, $x_2(t)$ comprise a real component and an imaginary component. In one embodiment, mixing the two frequency response signals comprises initially rotating the phase of one of the frequency response signals and scaling the real component and the imaginary component of one of the frequency response signals. As shown in equation (3) below, the response vector $x_2(t)$ is rotated by $\Delta\theta_n(t)$ to yield $x_2'(t)$.

$$f_2: \vec{x}_2'(t) = k_d(t) X_d(t) \angle (\theta_d(t) + \Delta\theta_d(t) - \Delta\theta_n(t)) + k_n(t) X_n(t) \angle \theta_n(t) \quad (3)$$

When $\Delta\theta_d(t) = \Delta\theta_n(t) = \theta(t)$ and $k_d(t) = k_n(t) = k(t)$, $x_2(t)$ becomes $k(t)x_1(t)$ with a phase rotation, this condition represents the "collinearity", namely that the eddy current response in X-Y plots at different frequencies is collinear after a phase angle rotation. In some embodiments, a time shift operation may also be performed on at least one of the frequency response signals.

A mixed frequency response signal is then obtained as shown in equation (4) by subtracting the first frequency response signal from a rotated and scaled second frequency response signal. As shown below, the rotated second frequency response signal $x_2'(t)$ is scaled by the coefficient $1/k_n(t)$ on both sides and subtracted by the frequency response signal $x_1(t)$ to obtain a mixed signal $x_{12}(t)$.

$$\text{Mixing } f_1 \text{ and } f_2: \vec{x}_{12}(t) = \vec{x}_2'(t)/k_n(t) - \vec{x}_1(t) \quad (4)$$
$$= \frac{k_d(t)}{k_n(t)} X_d(t) \angle (\theta_d(t) + \Delta\theta_d(t) - \Delta\theta_n(t)) - X_d(t) \angle \theta_d(t)$$

As can be seen, with the rotation and scaling operation, the noise factor in Eq. (4) is eliminated after the multifrequency mixing operation. As a result of the rotation and scaling operation, a noise-filtered response signal is generated based on the processing parameters. In general, this process minimizes a residual, which represents undesired noise features in the two frequency response signals, after the mixing operation.

In step 58, the processing parameters obtained from step 56 are applied to the entire multifrequency response signal dataset generated by equation (4) to generate a noise-filtered dataset. As will be appreciated by those skilled in the art, the resultant noise-filtered dataset comprises both real and imaginary components with improved signal to noise ratio.

In step 60, magnitude information and phase information are produced from the noise-filtered dataset. Further, in this step, a phase analysis is performed on the noise-filtered dataset, where an offset is applied to the horizontal component to suppress noise sensitivity. The data from the phase analysis contains information correlated with the defect, and provides additional discrimination to reduce false calls. As will be appreciated by those skilled in the art, when the phase changes are different ($\Delta\theta_d(t) \neq \Delta\theta_n(t)$) and the magnitude changes are different ($k_d(t) \neq k_n(t)$), the mixed signal, $x_{12}(t)$ represents a flaw signal with the undesired feature noise eliminated. In accordance with one embodiment, the phase $\theta(t)$ and its rotation $\Delta\theta(t)$ with frequency are functions of the probe position while scanning over the flaw. As a result, the residual between the noise terms in equations (1) and (2) is substantially reduced but not necessarily zero at different positions or time (t) after multi-frequency mixing, and therefore the mixed signal retains desired flaw signals and provides an improved signal to noise ratio.

The technique for performing subsurface or blind zone defect inspections using the multifrequency phase analysis technique developed in accordance with the present technique enhances the signal to noise ratio and improves the near surface detection in deeper locations within the part to be inspected. In addition, the above technique can be used for a wide variety of applications, including, but not limited to, detecting defects in welds, wherein such defects can appear throughout the thickness of the weld or for conducting inspections in coated metallic parts, such as, a seal tooth with a wear-resistant coating, where the inspection of the part has to be conducted without removing the conductive coating. The above technique can also be used for measuring defects in the blind zone in billets, where the blind zone is in a range between 0–0.0060 inches (or about 0–0.1524 mm).

As will be appreciated by those skilled in the art, the embodiments and applications illustrated and described above will typically include or be performed by appropriate executable code in a programmed computer or hardware electronics. Such programming will comprise a listing of executable instructions for implementing logical functions. The listing can be embodied in any computer-readable medium for use by or in connection with a computer-based system that can retrieve, process and execute the instructions.

In the context of the present technique, the computer-readable medium is any means that can contain, store or transport the instructions. The computer readable medium can be an electronic, a magnetic, an optical, an electromagnetic, or an infrared system, apparatus, or device. An illustrative, but non-exhaustive list of computer-readable mediums can include an electrical connection (electronic) having one or more wires, a portable computer diskette (magnetic), a random access memory (RAM) (magnetic), a read-only memory (ROM) (magnetic), an erasable programmable read-only memory (EPROM or Flash memory) (magnetic), an optical fiber (optical), and a portable compact disc read-only memory (CDROM) (optical).

The technique for performing subsurface or blind zone defect inspections using the multifrequency phase analysis technique disclosed herein is further illustrated in the following non-limiting examples.

EXAMPLES

Figure 5:
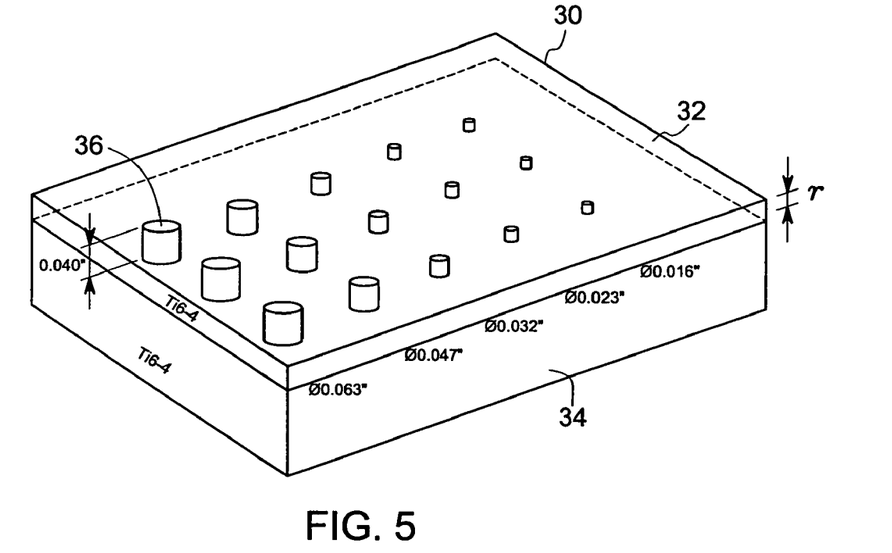
FIG. 5 is an illustration of an exemplary inspection part containing a number of holes representing subsurface defects.

As described herein, multifrequency phase analysis was applied to detect subsurface defects on an exemplary inspection part. FIG. 5 is an illustration of an exemplary inspection part containing a number of holes representing subsurface defects. The inspection part 30 is fabricated on Titanium 6-4 material and comprises a top plate 32 of thickness T and a 0.2" base plate 34. Three duplicated rows of flat bottom holes 36 of diameter 1/64", 1.5/64", 2/64", 3/64", 4/64" are introduced on the bottom of the top plate 32, with a spacing of half an inch between them. The flat bottom holes are 0.040" in height. The thickness T of the top plates, range from 0.050" to 0.10" and the flat bottom holes 36 are located at 0.010" to 0.060" beneath the top surface of the top plate 32.

Figure 6:
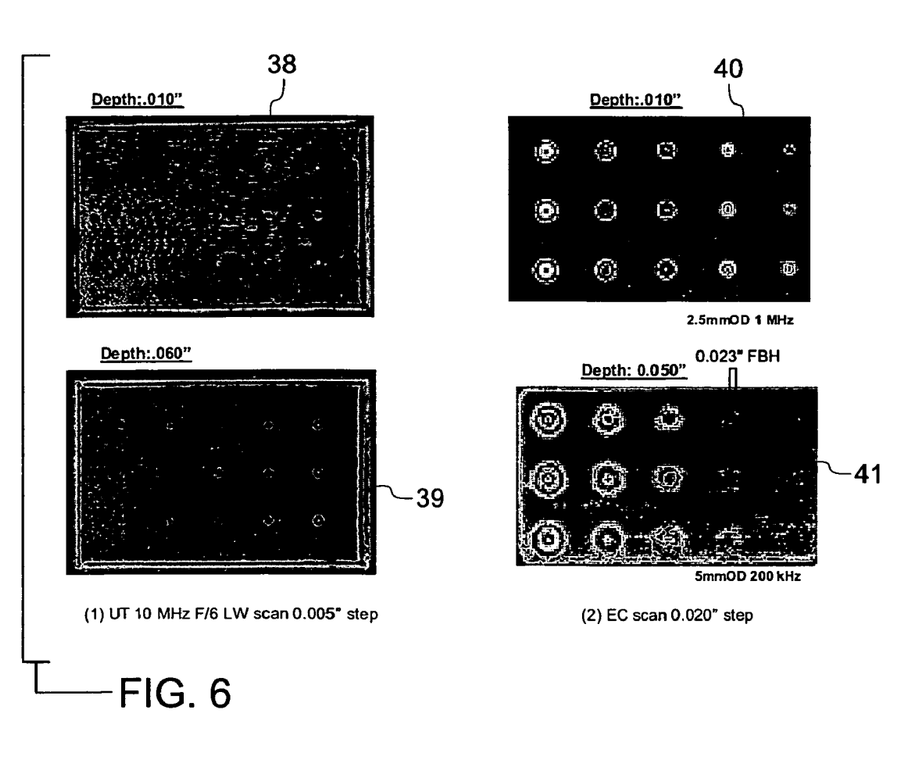
FIG. 6 depicts images generated as a result of the application of a single frequency eddy current on the exemplary inspection part illustrated in FIG. 5.

FIG. 6 depicts images generated as a result of the application of a single frequency eddy current on the exemplary inspection part illustrated in FIG. 5. A single frequency eddy current inspection was initially conducted with the benchmark of ultrasound inspection. It was observed that 10 MHz conventional ultrasound has a good detection capability for all sizes of flat bottom holes, which are 0.060" or deeper (shown in image 39). For flat bottom holes that are 0.010" deep, the detection of flaws using ultrasound proves to be inadequate (shown in image 38), compared to an eddy current inspection at 1 MHz (shown in image 40). The eddy current inspection with an absolute probe can barely detect a 0.023" flat bottom hole at a depth of 0.050", even with a probe diameter of 5 mm (shown in image 41). As will be appreciated by those skilled in the art, the detection of subsurface defects may be based on a number of factors such as the particular frequency range that is applied to the inspection part, the probe size and the probe sensitivity. A lower frequency and larger probe is generally capable of deeper penetrations within the part to be examined. A higher frequency yields a better eddy current sensitivity and a lower frequency yields a lower eddy current response. Furthermore, the size of the probe also has an effect on the sensitivity and resolution.

Figure 7:
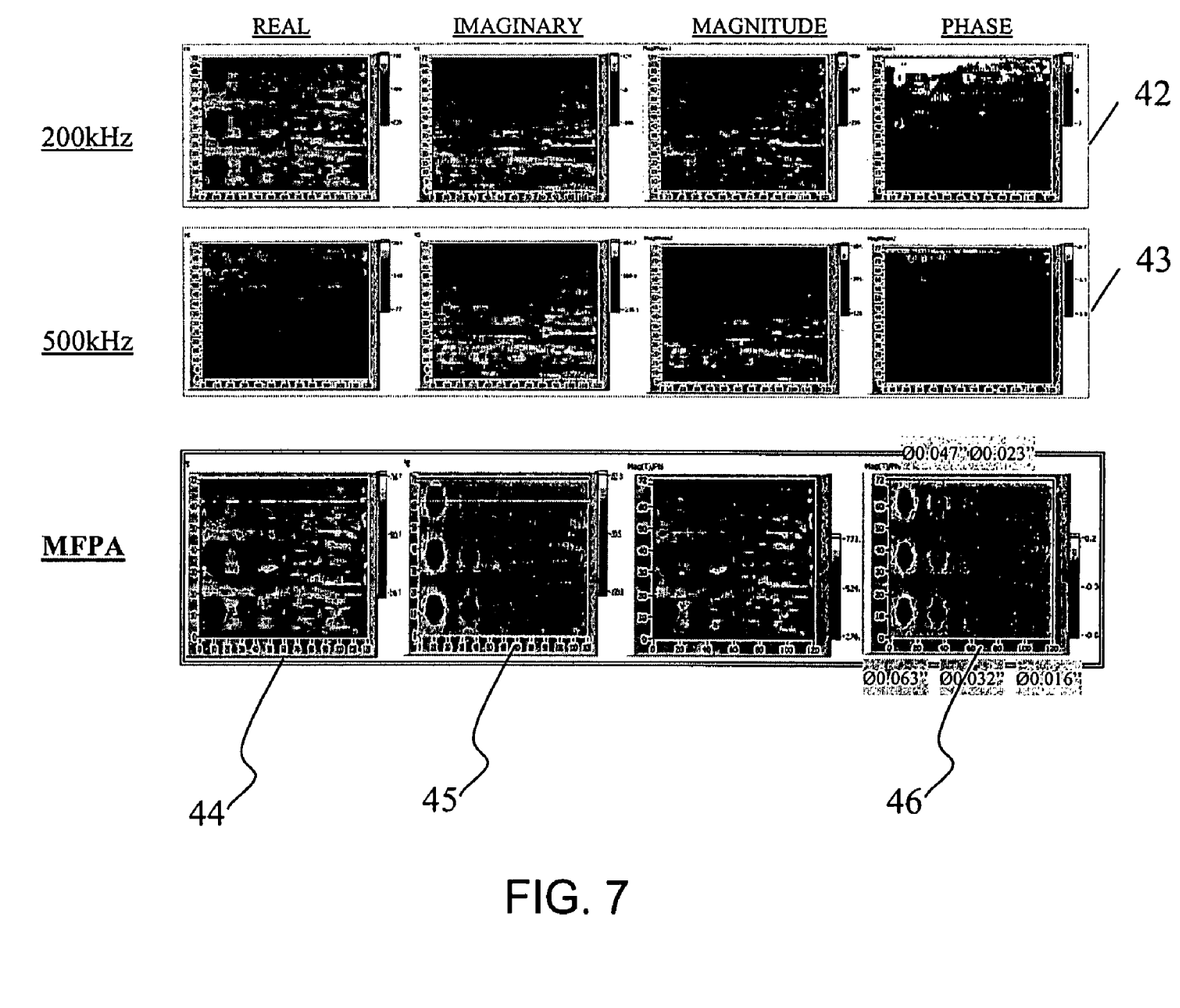
FIG. 7 depicts images generated as a result of the application of a multifrequency phase analysis on the exemplary inspection part illustrated in FIG. 5.

FIG. 7 depicts images generated as a result of the application of a multifrequency phase analysis on the exemplary inspection part illustrated in FIG. 5. A multi-frequency eddy current evaluation of the part under inspection was performed using a probe of 5 mm in diameter. Experiments were conducted on the inspection part using frequencies of 500 kHz and 200 kHz. Based on the conductive properties of the inspection part, the corresponding skin depth at 500 kHz and 200 kHz was approximately 0.036" and 0.058" respectively, which covered the range of the 0–0.050" of the depth of the blind zone. The phase difference between the two frequency responses for a flaw at a depth of 0.050" can be calculated to be approximately 189 degrees, which substantiates the criteria stated above, which is that $\Delta\theta_d(t)-\Delta\theta_n(t)$ is in a range from about 135° to about 225°. This criterion maximizes the mixed signal in Equation (4). For other noise features within the 50 mil zone, the phase difference is smaller in locations closer to the surface, and the yield gets relatively suppressed. As may be further observed, the signal to noise ratio in the multi-frequency real component image 44 or imaginary component image 45 is improved compared to images run at single frequencies, 200 kHz (shown in image 42) or 500 kHz (shown in image 43). The signal to noise ratio in the MFPA phase image 46 shown in FIG. 7 is improved because further phase discrimination is obtained, after the noise reduction of real and imaginary components with multi-frequency mixing, in contrast to the phase images 42 and 43 generated with the single frequency eddy currents 200 kHz or 500 kHz as shown in FIG. 7. It was also observed that at a depth of 50 mil, a 500 kHz eddy current has a poor sensitivity for those flat bottom holes. It was further observed that with a frequency 200 kHz, deeper penetration renders better detection at a depth of 50 mil than at 500 kHz. As may be observed from FIG. 7, the multifrequency phase analysis technique developed in accordance with the present invention reduces overall noise due to material variation and other noise. It was also observed that the smallest 0.016" flat bottom hole under a depth of 50 mils was detectable in FIG. 7, using the multifrequency phase analysis technique.

Figure 8:
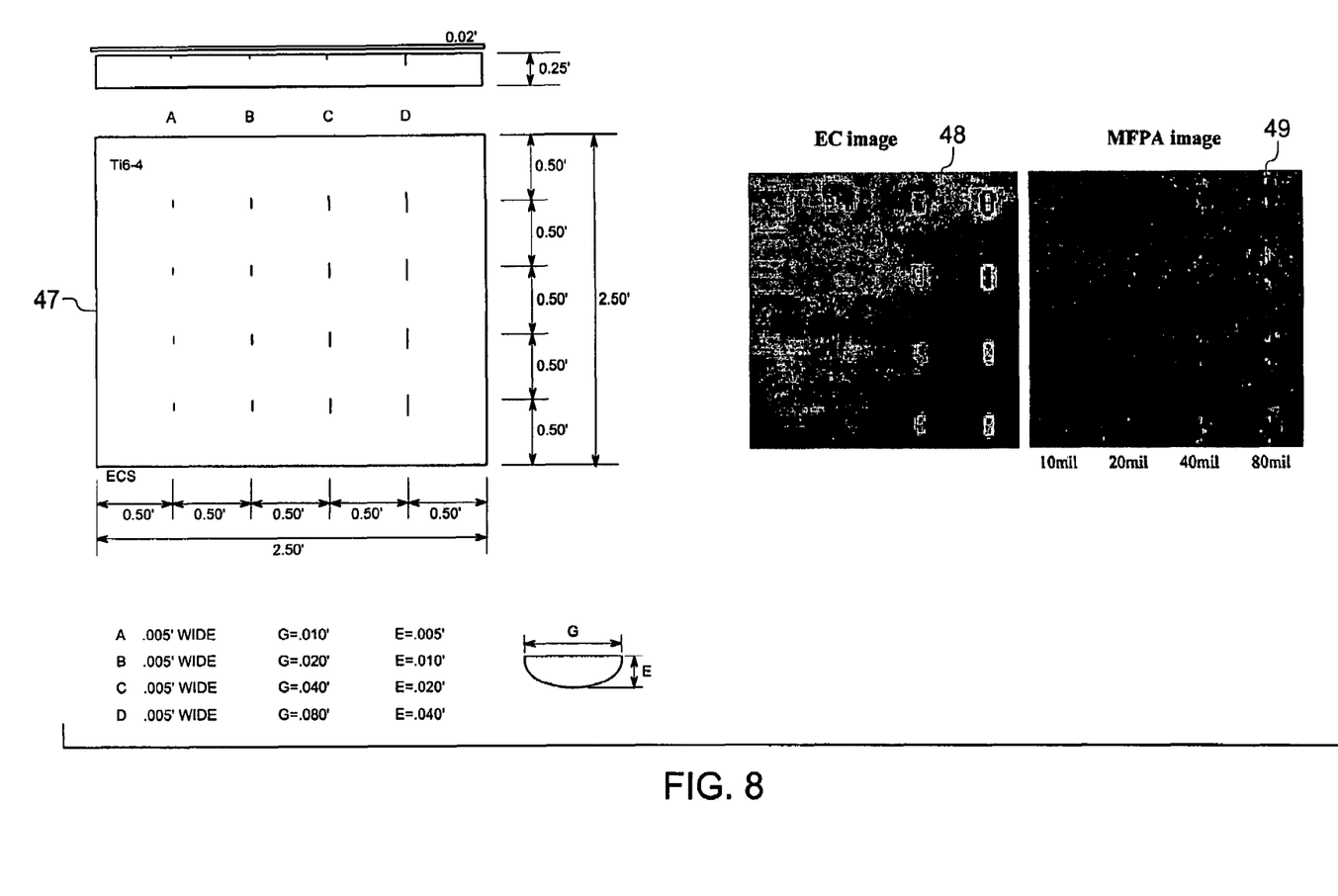
FIG. 8 is an illustration of the detection of a subsurface crack on an exemplary inspection part, using multifrequency phase analysis.

FIG. 8 is an illustration of the detection of a subsurface crack in an exemplary inspection part, using multifrequency phase analysis. Reference numeral 47 shows an exemplary inspection part. Reference numeral 48 shows an image generated as a result of the application of a single frequency eddy current on the inspection part 47. Reference numeral 49 shows an image generated as a result of the application of a multi-frequency phase analysis on the inspection part 47. As may be observed, the signal to noise ratio in the MFPA image 49 is improved as compared to the single frequency eddy current image 48.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed:

1. A method for inspecting a part, the method comprising:
applying a plurality of multifrequency excitation signals to a probe to generate a plurality of multifrequency response signals for the part being inspected;
and performing a multifrequency phase analysis on the multifrequency response signals,
wherein the probe is an eddy current probe, wherein the applying step induces a plurality of eddy currents in the part, wherein the multifrequency response signals are generated by the eddy currents induced in the part with the eddy current probe, and wherein performing the multifrequency phase analysis comprises:
identifying a reference dataset, wherein the reference dataset comprises at least two frequency response signals, and wherein the at least two frequency response signals comprise distinct frequency ranges;

mixing the at least two frequency response signals to determine a plurality of processing parameters;

and applying the processing parameters to a multifrequency response signal dataset to generate a noise-filtered dataset, the method further comprising:

using the multifrequency phase analysis to inspect a subsurface of the part.

2. The method of claim 1, comprising selecting a plurality of frequencies for the multifrequency signals such that $\Delta\theta_d(t)-\Delta\theta_n(t)$ is in a range from about 135° to about 225° wherein $\Delta\theta_d(t)$ is a phase change of a flaw response, and wherein $\Delta\theta_n(t)$ is the phase change of a noise feature.

3. The method of claim 1, wherein each of the frequency response signals comprises a real component and an imaginary component, and wherein mixing the at least two frequency response signals comprises rotating the phase of at least one frequency response signal.

4. The method of claim 3, further comprising scaling the real component and scaling the imaginary component of at least one frequency response signal.

5. The method of claim 3, further comprising performing a time-shift operation on at least one of the frequency response signals.

6. The method of claim 3, further comprising minimizing a residual corresponding to the processing parameters, wherein the residuals represent undesired noise features in the at least two frequency response signals.

7. The method of claim 1, wherein mixing the at least two frequency response signals comprises subtracting a first frequency response signal from a rotated and scaled second frequency response signal.

8. The method of claim 1, further comprising performing a phase analysis on the noise-filtered dataset, wherein the phase analysis comprises obtaining phase information and magnitude information associated with the noise filtered dataset.

9. A method for performing subsurface defect inspections using eddy currents, the method comprising:
applying a plurality of multifrequency signals to an eddy current probe;
generating a plurality of multifrequency response signals from the plurality of multifrequency signals, wherein the plurality of multifrequency response signals are included in a multifrequency response dataset;
identifying a reference free dataset comprising at least two frequency response signals, wherein the reference free dataset is a subset of the multifrequency response dataset, and wherein the at least two frequency signals comprise distinct frequency ranges;
mixing the at least two frequency response signals to determine a plurality of processing parameters;
applying the plurality of processing parameters to the multifrequency response signal dataset to generate a noise-filtered image dataset;
performing a phase analysis on the noise-filtered dataset, and using the noise filtered dataset to inspect a subsurface of a part.

10. The method of claim 9, comprising selecting a plurality of frequencies to generate the plurality of multifrequency signals.

11. The method of claim 9, wherein mixing the at least two frequency response signals comprises rotating the phase of at least one frequency response signal and scaling the real component and scaling the imaginary component of at least one frequency response signal.

12. The method of claim 9, further comprising minimizing the residual corresponding to the processing parameters, wherein the residuals represent undesired noise features in the at least two frequency response signals.

13. The method of claim 9, wherein mixing the at least two frequency response signals comprises subtracting a first frequency response signal from a rotated and scaled second frequency response signal.

14. The method of claim 9, wherein the phase analysis comprises obtaining phase information and magnitude information associated with the noise-filtered dataset.

15. An inspection system comprising:
an eddy current probe configured to induce eddy currents in a part, for performing an inspection of the part;
an eddy current instrument coupled to the eddy current probe, wherein the eddy current instrument is configured to apply a plurality of multifrequency excitation signals to the eddy current probe to generate a plurality of multifrequency response signals; and
a processor configured to analyze the multifrequency response signals from the eddy current instrument by performing a multifrequency phase analysis, to inspect a subsurface of the part, wherein the processor is further configured to:
identify a reference dataset, wherein the reference dataset comprises at least two frequency response signals, and wherein the at least two frequency response signals comprise distinct frequency ranges;
mix the at least two frequency response signals to determine a plurality of processing parameters; and
apply the processing parameters to a multifrequency response signal dataset to generate a noise-filtered dataset.

16. The system of claim 15, wherein the eddy current probe is mounted on a scanner, and wherein the scanner is configured to move the probe relative to the part, for inspection of the part.

17. The system of claim 15, wherein the multifrequency response signals are related to the eddy currents induced in the part by the eddy current probe.

18. The system of claim 15, wherein each of the frequency response signals comprises a real component and an imaginary component, and wherein the processor is further configured to rotate the phase of at least one frequency response signal.

19. The system of claim 15, wherein the processor is configured to minimize a residual corresponding to the processing parameters, and wherein the residuals represent undesired noise features in the at least two frequency response signals.

20. The system of claim 15, wherein the processor is configured to perform a phase analysis on the noise-filtered dataset, and wherein the phase analysis comprises obtaining phase information and magnitude information associated with the noise filtered dataset.

21. A computer-readable medium storing computer instructions for instructing a computer system for performing subsurface defect inspections, the computer instructions comprising:
applying a plurality of multifrequency signals to an eddy current probe to generate a plurality of multifrequency response signals, wherein the plurality of multifrequency response signals are included in a multifrequency response dataset;
identifying a reference dataset comprising at least two frequency response signals, wherein the reference dataset is a subset of the multifrequency response dataset, and wherein the at least two frequency signals comprise distinct frequency ranges;

mixing the at least two frequency response signals to determine a plurality of processing parameters;

applying the plurality of processing parameters to the multifrequency response signal dataset to generate a noise-filtered dataset;

performing a phase analysis on the noise-filtered image dataset;

and using the noise-filtered dataset to inspect a subsurface of a part.

* * * * *